United States Patent [19]
Dorr et al.

[11] Patent Number: 6,060,083
[45] Date of Patent: May 9, 2000

[54] TOPICAL DMSO TREATMENT FOR PALMAR-PLANTAR ERYTHRODYSETHESIA

[75] Inventors: Robert T. Dorr; David S. Alberts, both of Tucson, Ariz.

[73] Assignee: Topical Technologies, Inc., Tuscon, Ariz.

[21] Appl. No.: 09/283,208

[22] Filed: Apr. 1, 1999

[51] Int. Cl.$^7$ .......................... A61K 31/10; A61K 9/127
[52] U.S. Cl. ............................ 424/450; 514/708
[58] Field of Search ............................ 424/450; 514/708, 514/870, 871

[56] References Cited

U.S. PATENT DOCUMENTS 5,891,875 4/1999 Hipskind .............................. 514/235.2

OTHER PUBLICATIONS

Bertelli, G., et al., Topical Dimethylsulfoxide for the Prevention of Soft Tissue Injury After Extravasation of Vesicant Cytotoxic Drugs: A Prospective Clinical Study. *J. Clin. Oncol.* 13: 2851, 1995.

Blum, R.H., et al., A New Anticancer Drug with Significant Clinical Activity. *Ann. Intern. Med.* 80: 249, 1974.

Comandone, A., et al., Palmar–Plantar Erythrodysestasia Syndrome Associated With 5–Fluorouracil Treatment. *Anticancer Res.* 13: 1781, 1993.

Fabian, C.J., et al., Pyridoxine Therapy for Palmar–Plantar Erythrodysesthesia Associated With 5–Fluorouracil Infusion. *Invest. New Drugs* 8: 57, 1990.

Frei, E., et al., Dose: A Critical Factor in Cancer Chemotherapy. *Am. J. Med.* 69: 585, 1980.

Gabizon, A., et al., Liposome Formulation with Prolonged Circulation Time in Blood and Enhanced Uptake by Tumors. *Proc. Natl. Acad. Sci. U S A* 85: 6949, 1988.

Gordon, K.B., et al., Hand–Foot Syndrome Associated with Liposome–Encapsulated Doxorubicin Therapy. *Cancer* 75: 2169,1995.

Henderson, I.C., et al., Dose–Response in the Treatment of Breast Cancer: A Critical Review. *J. Clin. Oncol.* 6: 1501, 1988.

James, N.D., et al., Liposomal Doxorubicin (Doxil): An Effective New Treatment for Kaposi's Sarcoma in AIDS. *Clin. Oncol. (R. Coll. Radiol.)* 6: 294, 1994.

Larson, D.L., Treatment of Tissue Extravasation by Antitumor Agents. *Cancer* 49: 1796, 1982.

Leichman, C.G., et al., Prolonged Continuous Infusion of Fluorouracil with Weekly Bolus Leucovorin: A Phase II Study in Patients with Disseminated Colorectal Cancer. *J. Natl. Cancer Inst.* 85: 41, 1993.

Levine, L.E., et al., Distinctive Acral Erythema Occurring During Therapy for Severe Myelogenous Leukemia. *Arch. Dermatol.* 121: 102, 1985.

Lipschultz, S.E., et al., Late Cardiac Effects of Doxorubicin Therapy for Acute Lymphoblastic Leukemia in Childhood. *N. Engl. J. Med.* 324: 808, 1991.

Lokich, J.J., et al., Chemotherapy–Associated Palmar–Plantar Erythrodysesthesia Syndrome. *Ann. Intern. Med.* 101: 798, 1984.

Lokich, J.J., et al., A Prospective Randomized Comparison of Continuous Infusion Fluorouracil with a Conventional Bolus Schedule in Metastatic Colorectal Carcinoma: A Mid–Atlantic Oncology Program Study. *J. Clin. Oncol.* 7: 425, 1989.

Muggia, F.M., et al., Phase II Study of Liposomal Doxorubicin in Refractory Ovarian Cancer: Antitumor Activity and Toxicity Modification by Liposomal Encapsulation. *J. Clin. Oncol.* 15: 987, 1997.

Northfelt, D.W., et al., Doxorubicin Encapsulated In Liposomes Containing Surface–Bound Polyethylene Glycol: Pharmacokinetics, Tumor Localization, and Safety in Patients with AIDS–Related Kaposi's Sarcoma. *J. Clin. Pharmacol.* 36: 55, 1996.

Olver, I.N., et al., A Prospective Study of Topical Dimethyl Sulfoxide for Treating Anthracyline Extravasation. *J. Clin. Oncol.* 6: 1732, 1988.

Papahadjopoulos, D., et al., Sterically Stabilized Liposomes: Improvements in Pharmacokinetics and Antitumor Therapeutic Efficacy. *Proc. Natl. Acad. Sci. U S A* 88: 11460, 1991.

Simpson, J.K., et al., Liposomal Doxorubicin for Treatment of AIDS–Related Kaposi's Sarcoma. *Clin. Oncol. (R. Coll. Radiol.)* 5: 372, 1993.

Uziely, B., et al., Liposomal Doxorubicin: Antitumor Activity and Unique Toxicities During Two Complementary Phase I Studies. *J. Clin. Oncol.* 13: 1777, 1995.

Vogelzang, N.J., et al., Cancer Chemoptherapy and Skin Changes. *Ann. Intern. Med.* 103: 303, 1985.

VonHoff, D.D., et al., Risk Factors for Doxorubicin–Induced Congestive Heart Failure. *Ann. Intern. Med.* 91: 710, 1979.

Wiernik, P.H., et al., Hexamethylmelamine and Low or Moderate Dose Cisplatin With or Without Pyridoxine for Treatment of Advanced Ovarian Carcinoma: A Study of the Eastern Cooperative Oncology Group. *Cancer Invest.* 10: 1, 1992.

FDA's List of Orphan Products Designations and Approvals, p. 24 (through Dec. 31, 1998).

Alberts, D.S., et al., Safety Aspects of Pegylated Liposomal Doxorubicin in Patients with Cancer. *Drugs*, 54 (suppl. 4): 30–35, 1997.

Brown, V.K., et al., A Note on the Toxicity and Solvent Properties of Dimethyl Sulphoxide. *J. Pharmacy Pharmacol.*, 15: 688–692, 1963.

Caujolle F.M.E., et al., Limits of Toxic and Teratogenic Tolerance of Dimethyl Sulfoxide. *Ann. N.Y. Acad. Sci.*, 141: 110–125, 1967.

David, N.A., The Pharmacology of Dimethyl Sulfoxide 6544. *Ann. Rev. Pharmacology*, 12: 353–374, 1972.

(List continued on next page.)

*Primary Examiner*—Gollamudi S. Kishore
*Attorney, Agent, or Firm*—Marshall, O'Toole, Gerstein, Murray & Borun

[57] ABSTRACT

A method for treating palmar-plantar erythrodysethesia syndrome includes applying to affected areas a therapeutically effective amount of a dimethyl sulfoxide solution.

6 Claims, No Drawings

OTHER PUBLICATIONS

Desai, M.H., et al., Prevention of Doxorubicin–Induced Skin Ulcers in the Rat and Pig with Dimethyl Sulfoxide (DMSO). *Cancer Treat. Rep.*, 66: 1371–1374, 1982.

Gabizon, A., et al., Clinical Studies of Liposome–Encapsulated Doxorubicin. *Acta. Oncologica*, 33: 779–786, 1994.

Garnick, M., et al., Persistence of Anthracycline Levels Following Dermal and Subcutaneous Adriamycin Extravasation. *Proc. AACR*, 22: 173, 1981.

Gerhards, E., et al., THe Metabolism of Dimethyl Sulfoxide and Its Metabolic Effects in Man and Animals. *Ann. N.Y. Acad. Sci.*, 141: 65–76, 1967.

Hucker, H.B., et al., Physiological Disposition and Metabolism of Dimethyl Sulfoxide (DMSO). *Fed. Proc.*, 24: 546, 1965.

Hucker, H.B., et al., Absorption, Distribution and Metabolism of Dimethylsulfoxide in the Rat, Rabbit and Guinea Pig. *J. Pharmacol. Exp. Ther.*, 154: 176–184, 1966.

Hucker, H.B., et al., Studies in the Absorption, Excretion and Metabolism of Dimethylsulfoxide (DMSO) in Man. *J. Pharmacol. Exp. Ther.*, 155: 309–317, 1967.

Klingman, A.M., Topical Pharmacology and Toxicology of Dimethyl Sulfoxide—Part I. *J. Amer. Med. Assoc.*, 193: 140–148, 1965.

Kolb, K.H., et al., Absorption, Distribution, and Elimination of Labeled Dimethyl Sulfoxide in Man and Animals. *Ann. N.Y. Acad. Sci.*, 141: 85–95, 1967.

Larson, D.L., What is the Appropriate Management of Tissue Extravasation by Antitumor Agent? *Plast. Reconstruct. Surg.*, 75: 397–405, 1985.

Lebredo, L., et al., DMSO Protects Against Adriamycin–Induced Tissue Necrosis. *J. Surg. Res.*, 53: 62–65, 1992.

MacGregor, W.S., The Chemical and Physical Properties of DMSO. *Ann. N.Y. Acad. Sci.*, 141: 3–12, 1967.

National Technical Information Service (NTIS): Dimethyl Sulfoxide as a Therapeutic Agent FDA contract FDA 70–22, 1972.

Nobbs, P., et al., Soft–Tissue Injury Caused by Antineoplastic Drugs is Inhibited by Topical Dimethyl Sulphoxide and Alpha Tocopherol. *Br. J. Cancer*, 48: 873–876, 1983.

Northfelt, D.W., et al., Randomized Comparative Trial of Doxil® vs. Adriamycin, Bleomycin, and Vincristine (ABV) in the Treatment of Severe AIDS–Related Kaposi's Sarcoma (AIDS–KS). 3rd Conference on Retroviruses and Opportunistic Infections, abst 379, 1996.

Okano, T., et al., Doxorubicin–Induced Skin Ulcer in the Piglet. *Cancer Treat. Rep.*, 67: 1075–1078, 1983.

Porche, D.J., Liposomal Doxorubicin (Doxil®). *JANAC*, 7: 55–59, 1996.

Shirley, H.H., et al., Lack of Ocular Changes with Dimethyl Sulfoxide Therapy of Scleroderma. *Pharmacotherapy*, 9: 165–168, 1988.

Smith, E.R., et al., The Single—and Repeated—Dose Toxicity of Dimethyl Sulfoxide. *Ann. N.Y. Acad. Sci.*, 141: 96–109, 1967.

Soble, M.J., et al., Dose–Dependent Skin Ulcers in Mice Treated with DNA Binding Antitumor Antibiotics. *Cancer Chemother. Pharmacol.*, 20: 33–36, 1987.

Svingen, B.A., et al., Protection Against Adriamycin–Induced Skin Necrosis in the Rat by Dimethyl Sulfoxide and α–Tocopherol. *Cancer Res.*, 41: 3395–3399, 1981.

VanSloten Harwood, K., et al., Evaluation of Dimethethyl Sulfoxide and Local Cooling as Antidotes for Doxorubicin Extravasation in a Pig Model. *Oncol. Nurs. Forum.*, 14: 39–44, 1987.

Willson, J.E., et al., A Toxicologic Study of Dimethyl Sulfoxide. *Toxicol. Appl. Pharmacol.*, 7: 104–112, 1965.

Working, P.K., et al., Pharmacological–Toxicological Expert Report: Caelyx™ (Stealth® Liposomal Doxorubicin HCI). *Hum. Exp. Toxicol.*, 15: 752–785, 1996.

Physicians Desk Reference, Doxil®(Doxorubicin HCI Liposome Injection, Sequus Pharmaceuticals). 2984–2988, 1999.

TOPICAL DMSO TREATMENT FOR PALMAR-PLANTAR ERYTHRODYSETHESIA

BACKGROUND OF THE INVENTION

1. Field of the Invention

The present invention relates to methods for treating a dermatologic syndrome known as hand-foot syndrome, or palmar-plantar erythrodysesthesia syndrome (PPES), which can be caused by chemotherapeutic regimens that utilize drugs such as capecitabine, 5-fluorouracil ("fluorouracil"), cytarabine, or doxorubicin.

2. Description of Related Art

Chemotherapeutic regimens that utilize drugs such as capecitabine, fluorouracil, cytarabine, and doxorubicin have been shown to cause a dermatologic syndrome known as hand-foot syndrome, or palmar-plantar erythrodysesthesia syndrome (PPES). [Comandone, et al., *Anticancer Res.* 13:1781 (1993); Fabian, et al., *Investigational New Drugs* 8:57 (1990); Gordon et al., *Cancer.* 75:2169 (1995); Lokich, et al., *Ann. Intern. Med* 101:798 (1984); Vogelzang, et al., *Ann. Intern. Med.* 103:303 (1985)]. PPES initially starts with dysesthesia (an abnormal feeling of discomfort with weight bearing or touch) in the hands and feet, followed by edema and erythema, and ultimately, fissuring and ulceration involving the fingers, toes, palms and plantar aspects of the feet. As the syndrome progresses, the patient may experience extreme pain when grasping objects or walking. Histologically the condition is marked by a thickened granular layer, marked hyperkeratosis with parakeratosis, and many apoptotic keratinocytes. Unlike many other inflammatory dematoses, the apoptotic cells are not associated with local lymphocytes. There may also be focal basilar vacuolization and a perivascular lymphocytic infiltrate, along with melanin incontinence in the papillary dermis. [See Gordon, et al., *Cancer* 75:2169, 2172 (1995). PPES may also affect areas of the body other than the hands and feet, for example areas of the skin to which pressure is applied, such as at the belt or bra line. The severity of PPES may be graded on a 0–3 scale. A grade of 0 indicates no PPES; grade 1 indicates mild PPES; grade 2 indicates moderate PPES; and grade 3 indicates severe PPES. [Fabian, et al., *Investigational New Drugs* 8:57 (1990)].

Doxorubicin, an anthracycline, is commonly administered for a wide range of solid tumors and hematologic malignancies. Liposomal doxorubicin preparations, which are made of small particles of doxorubicin encapsulated in hydrophilic lipid particle bilayers, have been investigated as safer and potentially more active alternatives to the parent compound. Polyethyleneglycol (PEG) coated liposome technology greatly alters the pharmacokinetics of doxorubicin with the PEG coating, resulting in major differences in doxorubicin clearance and distribution, along with significant increases in drug concentrations in tumors. Pegylated (PEG-coated) liposomal doxorubicin has proven effective in the treatment of AIDS-related Kaposi's sarcoma, ovarian cancer refractory to platinum and paclitaxel therapies, and metastatic breast cancer.

The incidence of severe PPES, as a result of pegylated liposomal doxorubicin therapy has been reported to be between 3.4% and 34%, depending on drug dose and schedule. [James, et al., *Clin. Oncol.* 6:294 (1994); Muggia, et al., *J. Clin. Oncol.* 15:987(1997); Northfelt, et al., *J. Clin. Pharmacol.* 36:55 (1996); Simpson et al., *Clin. Oncol.* 5:372 (1993); Uziely et al., *J. Clin. Oncol.* 13:1777 (1995)]. Although PPES is noted also to occur with prolonged administrations of other chemotherapeutic regimes, whether these drugs have a common mechanism for causing the syndrome is not known. [Comandone, et al., *Anticancer Res.* 13:1781 (1993); Fabian, et al., *Investigational New Drugs* 8:57 (1990); Gordon, et al., *Cancer* 75:2169 (1995); Leichman, et al., *J. Natl. Cancer Inst.* 85:41 (1993); Levine, et al., *Arch. Dermatol.* 121:102 (1985); Lokich, et al., *Ann. Intern. Med* 101:798 (1984); Lokich, et al., *J. Clin. Oncol.* 7:425 (1989); Vogelzang, et al., *Ann. Intern. Med* 103:303 (1985)].

Tissue extravasation reactions sometimes occur when chemotherapeutic agents inadvertently leak out of a blood vessel into which the drug is introduced, and into the surrounding tissue. Such reactions can cause severe injury to the surrounding tissue, often requiring plastic surgery, such as skin grafting, to repair the damaged tissue. This type of injury differs from PPES in that an extravasation reaction is a local injury caused by direct contact between a particular drug and affected tissue. PPES, on the other hand is a systemic reaction caused by a drug that is circulating in the bloodstream. PPES primarily affects the hands and feet of a patient, not the vicinity of the site at which the drugs are intravenously introduced into the patient.

Topical 99% (by weight, with 1% water) dimethyl sulfoxide (DMSO) has shown strong activity in treating tissue extravasation reactions that occur during intravenous administration of doxorubicin. [Bertelli et al., *J. Clin. Oncol.* 13:2851 (1995); Olver et al., *J. Clin. Oncol.* 6:1732 (1988)]. In a clinical study by Olver et al., 20 consecutive patients were treated with topical 99% DMSO for anthracycline soft tissue extravasation. Use of the 99% formulation four times daily for up to 14 days was shown to reduce doxorubicin soft tissue damage. At three months post DMSO treatment, 38% of the patients had no sign of residual damage and in 63% of the patients, only a pigmented, indurated skin lesion remained, without any sign of ulceration. Because no patients progressed to ulceration, the investigators documented a true ulceration range of 0–17% (95% confidence interval) compared to the 30% progression rate to ulceration observed by Larson [*Cancer* 49:1796 (1982)] when only ice was applied to the extravasation site. More recently, Bertelli et al. [*J. Clin. Oncol.* 13:2851] reported complete recovery from doxorubicin extravasation injury in 11 of 11 patients treated three times daily with 99% topical DMSO. DMSO is known to be rapidly absorbed through intact skin and mucous membranes. Additionally, DMSO has been reported to exert anti-inflammatory action, locoregional analgesic, and histamine-like vasodilatory effects. [David, *Ann. Rev. Pharmacology,* 12:353 (1972)].

Current methods for treating PPES include dose reduction, lengthening of the drug administration interval and ultimately, drug withdrawal. However, alteration in drug dose and schedule can compromise the efficacy of a particular treatment regimen, and contribute to suboptimal cancer treatment. [Frei, et al., *Am. J. Med* 69:585 (1980); Henderson et al., *J. Clin. Oncol.* 6:1501 (1988)]. For example, in the treatment of refractory epithelial cell ovarian cancers, Muggia et al. [*J. Clin. Oncol.* 15:987] utilized intravenous doses of pegylated liposomal doxorubicin, 50 mg/m$^2$ every 3 weeks. When grade 3 or 4 PPES toxicity was encountered, the dose was reduced to 40 mg/m$^2$. If grade 1 or 2 toxicity persisted beyond a three-week period, the administration interval was lengthened to 4 weeks. Grade 3 PPES was observed in 31% of patients (11 of 35) and required dose reductions and/or dose delay after a median of three therapy cycles.

Pyridoxine therapy has been utilized to alleviate the onset of PPES during treatment with fluorouracil infusions for metastatic colon cancer. [Fabian et al., *Investigational New Drugs*, 8:57 (1990)]. However, the addition of pyridoxine to the combination of altretamine plus cisplatin in state II-IV epithelial ovarian cancer patients resulted in a significant reduction in response duration (i.e., pyridoxine reduces the effectiveness of the chemotherapy treatment). [Wiernik et al., *Cancer Investigation*, 10:1]. Pyridoxine has been suggested for the management of pegylated liposomal doxorubicin-induced PPES in some phase II trials, but its effectiveness has not been demonstrated.

There is a need for improved methods for preventing and treating PPES that are safe and effective, and do not interfere with the effectiveness of other drugs being administered.

SUMMARY OF THE INVENTION

According to one aspect of the present invention, a method for treating palmar-plantar erythrodysethesia syndrome includes applying to affected areas a therapeutically effective amount of a dimethyl sulfoxide solution. The DMSO solution preferably has a concentration of between about 50% and 100%, more preferably about 99%, although lower concentrations are also expected to be effective. The PPES can be caused by use of capecitabine, fluorouracil, cytarabine, an anthracycline, doxorubicin, or pegylated liposomal doxorubicin. The DMSO solution may be applied to the affected areas about one to four times per day. Preferably, the DMSO solution may be applied about three times per day.

DETAILED DESCRIPTION OF THE INVENTION

The method of the invention was evaluated in patients who developed PPES during pegylated liposomal doxorubicin therapy. Discussed below are case reports of the first two patients treated with topical DMSO for PPES caused by pegylated liposomal doxorubicin.

As shown below, positive results were obtained from topical 99% DMSO (containing 1% water) applied to the palms and soles in two patients who developed grade 3 PPES while on pegylated liposomal doxorubicin. Contrary to other studies that suggest the efficacy of pyridoxine in the resolution of PPES in patients treated with fluorouracil, no protection was evident in these two patients, who developed grade 3 PPES while taking prophylactic pyridoxine therapy.

Other concentrations of DMSO are also expected to be effective. Preferably, a solution containing about 50% to 100% can be used. DMSO may also be effective when mixed with other solvents, such as ethanol, acetone, or ether. In addition, a sustained release formulation of DMSO could be developed, according to techniques known to those skilled in the art, and a sustained release formulation of DMSO could be effective in treating PPES and more convenient to use than a DMSO-water solution.

Despite the successful prior use of DMSO to treat doxorubicin-induced extravasation injuries, DMSO has not previously been used to treat PPES, and the successful use of DMSO to treat PPES is surprising, due to the differences between extravasation injuries and PPES. For liposomal-doxorubicin-induced PPES, the applicants believe that the PPES may result from the release of small amounts of doxorubicin from liposomes that lodge and rupture in microcapillaries (with standing and grasping pressure), releasing doxorubicin into the subcutaneous tissue of the palms and soles. DMSO may be effective in treating liposomal-doxorubicin-induced PPES because the DMSO may transport the free doxorubicin into the systemic circulation and/or act as an antioxidant, thereby preventing doxorubicin's toxic effects on the local soft tissues. DMSO is also expected to be effective in treating PPES caused by other cancer drugs, such as capecitabine, fluorouracil, cytarabine, or non-liposomal doxorubicin.

The following examples are presented for purposes of illustration and should not be construed as limiting the invention which is delineated in the claims.

EXAMPLE I

Patient Number One

A 47-year old Mexican female with metastatic leiomyosarcoma to the lung was undergoing treatment at the Arizona Cancer Center with pegylated liposomal doxorubicin at 50 mg/m$^2$ infused over 1 hour every four weeks. The patient subsequently developed grade 1 palmar-plantar erythrodysethesia with swelling and light discoloration of hands and feet (without evidence of desquamation) prior to administration of the third course of chemotherapy. Despite the use of pyridoxine, 50 mg t.i.d. (three times daily), during the four weeks following her third treatment cycle, PPES increased in severity to grade 3 with swelling, erythema, pain and mild desquamation on her hands, as well as blisters on the dorsal aspects of the toes and the left anterior aspect of the wrist. She was seen in the Arizona Cancer Center, at the time of the scheduled fourth treatment, and was instructed to apply 99% DMSO (Burdick & Jackson Div., Baxter Healthcare, Muskegon, Mich.; HPLC-Grade) four times daily to the affected areas, delaying her fourth treatment cycle for one week. One week later, the patient was found to be without ulcers or blisters; however, mild skin desquamation remained on her hands and fingers. Pegylated liposomal doxorubicin therapy was continued at 50 mg/m$^2$ every four weeks for two additional four-week cycles. The signs and symptoms of PPES completely resolved by the time of the fifth course of pegylated liposomal doxorubicin while continuing topical 99% DMSO treatment.

EXAMPLE II

Patient Number Two

A 66-year old white male with a history of metastatic melanoma (lymph node, skin and lung metastases) received the first cycle of pegylated liposomal doxorubicin, 50 mg/m$^2$ every four weeks plus pyridoxine 50 mg p.o. (orally) t.i.d. A second cycle was administered without incident. At the time of the third cycle of chemotherapy, the patient reported a rash, lasting approximately one week, on his back, arms and groin, associated with erythema and mild pruritis without desquamation (i.e., grade 1 skin toxicity). When he returned to the Arizona Cancer Center for his fourth therapy cycle, he had a severe rash on his buttocks, hands and feet and was unable to walk, because of grade 3 PPES, with skin edema, erythema, blistering and desquamation on his soles. Pegylated liposomal doxorubicin therapy was held, pending resolution of the severe PPES, and the patient was instructed to apply topical 99% DMSO q.i.d. (four times daily) to his palms and soles. At his next clinic visit nine days later, there was resolution of sole edema allowing him to walk and skin erythema and desquamation was improved to grade 1–2 in severity. Although pegylated liposomal doxorubicin therapy was not readministered, at patient's request, due to fatigue, topical DMSO therapy was continued. Three weeks later, there was almost complete resolution of the PPES.

We claim:

1. A method for treating palmar-plantar erythrodysethesia syndrome comprising:

topically applying to affected areas a therapeutically effective amount of a dimethyl sulfoxide solution.

2. The method of claim 1 wherein the dimethyl sulfoxide solution has a concentration of about 50% to 100%.

3. The method of claim 2, wherein the dimethyl sulfoxide solution has a concentration of about 99%.

4. The method of claim 1, wherein the palmar-plantar erythrodysethesia syndrome is caused by use of capecitabine, fluorouracil, cytarabine, an anthracycline, doxorubicin, or pegylated liposomal doxorubicin.

5. The method of claim 4, wherein the palmar-plantar erythrodysethesia syndrome is caused by use of pegylated liposomal doxorubicin.

6. The method of claim 1 wherein the dimethyl sulfoxide solution is applied at a frequency of about one to four times per day.

* * * * *